United States Patent
Zwingenberger

[11] Patent Number: 6,030,214
[45] Date of Patent: Feb. 29, 2000

[54] MANUAL DEVICE FOR DELIVERING A VISCOUS FLUID

[76] Inventor: Arthur Zwingenberger, Rigistr. 36, 6006 Luzern, Switzerland

[21] Appl. No.: 09/169,485

[22] Filed: Oct. 9, 1998

[30] Foreign Application Priority Data

Oct. 15, 1997 [DE] Germany .......................... 197 45 567

[51] Int. Cl.[7] .............................. A61C 1/10; A61C 17/02
[52] U.S. Cl. .................................. 433/82; 433/80; 433/81
[58] Field of Search .................................. 433/80, 81, 82, 433/83, 84, 85, 86, 87, 88, 89, 90; 222/263, 333

[56] References Cited

U.S. PATENT DOCUMENTS 3,989,952 11/1976 Hohmann .
4,493,646 1/1998 Lacour et al. .

FOREIGN PATENT DOCUMENTS

2339827 A1 8/1973 Germany .
3103610 A1 2/1981 Germany .
3122061 A1 6/1981 Germany .
3129348 A1 7/1981 Germany .
3227417 A1 7/1982 Germany .

*Primary Examiner*—Nicholas D. Lucchesi
*Attorney, Agent, or Firm*—Nims, Howes, Collison, Hansen & Lackert

[57] ABSTRACT

The invention pertains to a device (10) for delivering a viscous fluid. The device features a housing (14), pistons (58,60) which act on containers (22,24) having the viscous fluid therein, a rotational drive unit (12) which moves the pistons (58,60) in a translational sense in the direction of a flow channel open towards the containers (22,24). The drive unit is arranged in a motor housing (81) separate from the housing (14). A gear assembly (68,70,72,76) converts the rotational drive motion into a translational motion of the pistons (58,60) towards a flow channel (52) which connects to a nozzle (30) and the delivery opening in the container (22,24). A coupling (82) is provided by which the rotational drive unit (12) can be decoupled from the gear assembly (68,70,72,76).

17 Claims, 8 Drawing Sheets

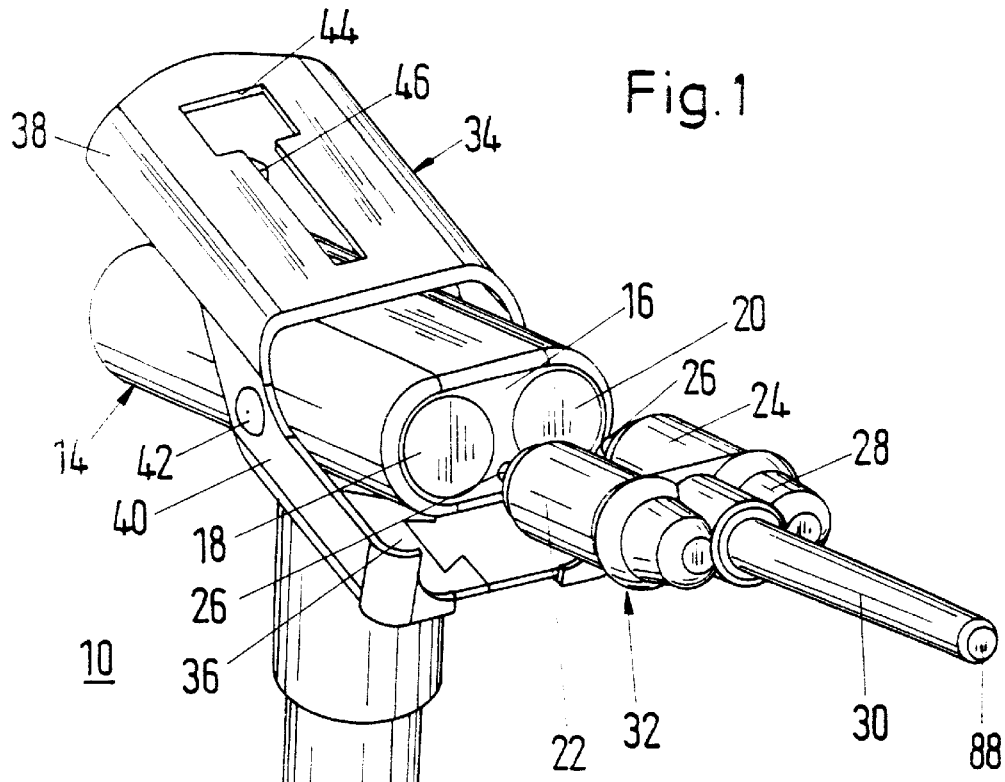
Fig. 1
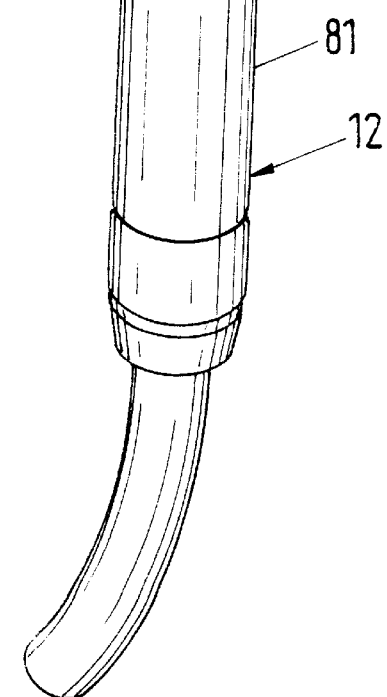
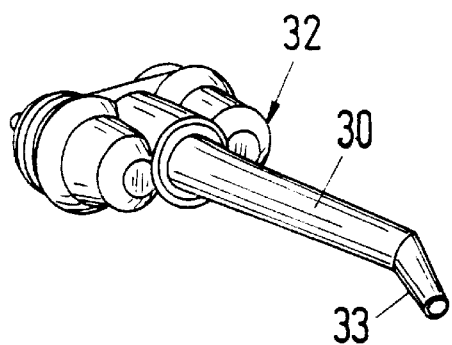
Fig. 2

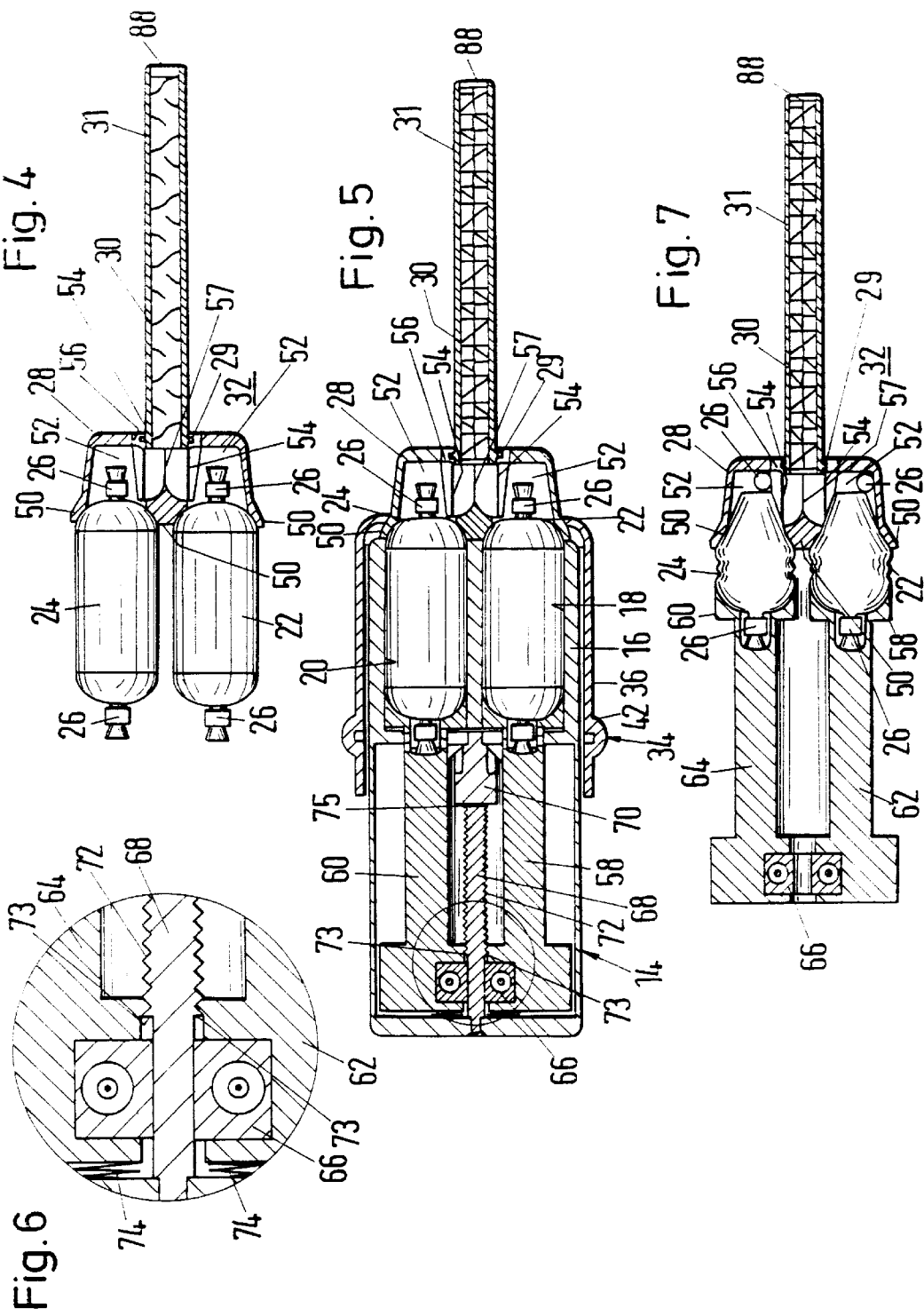

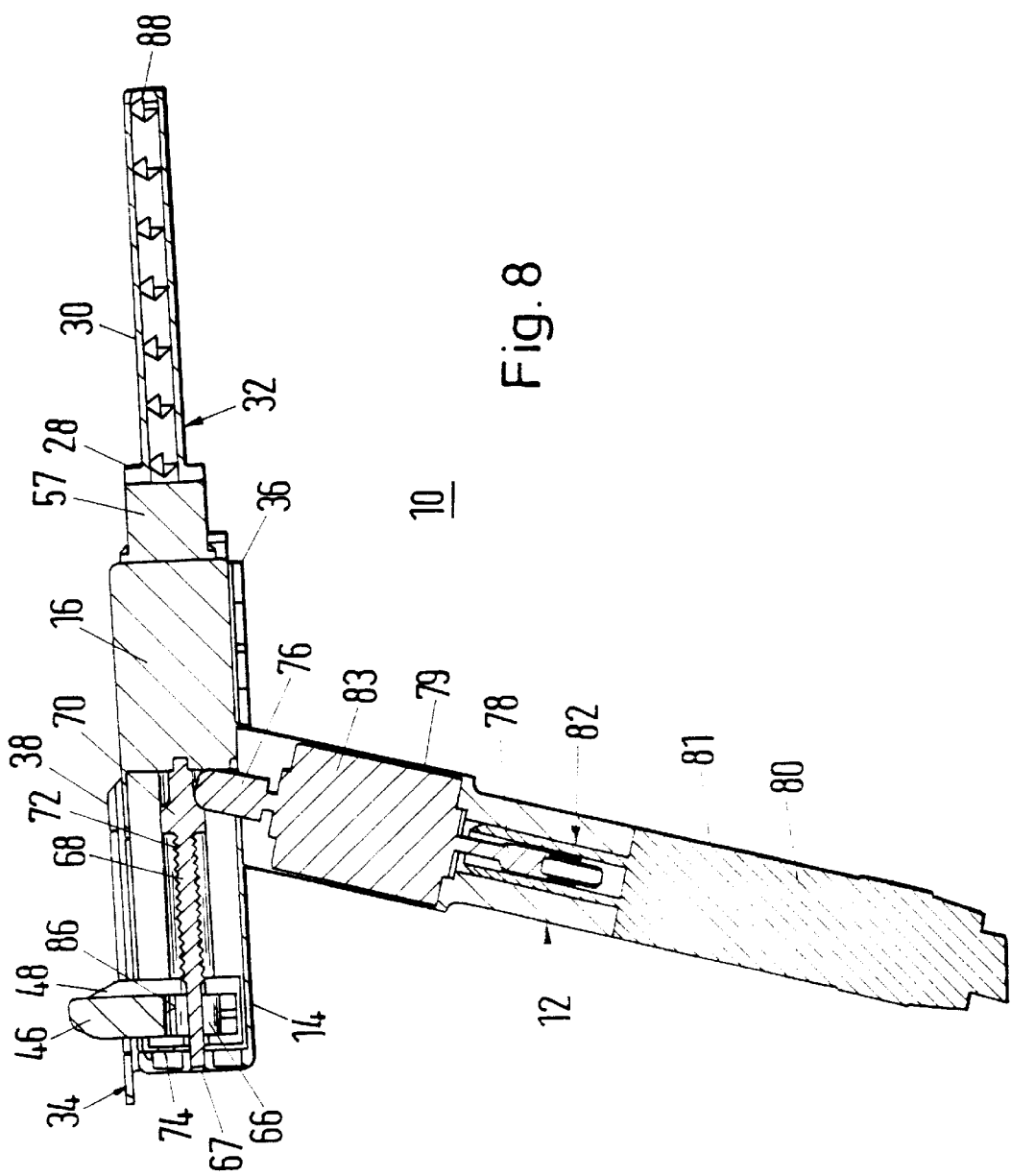

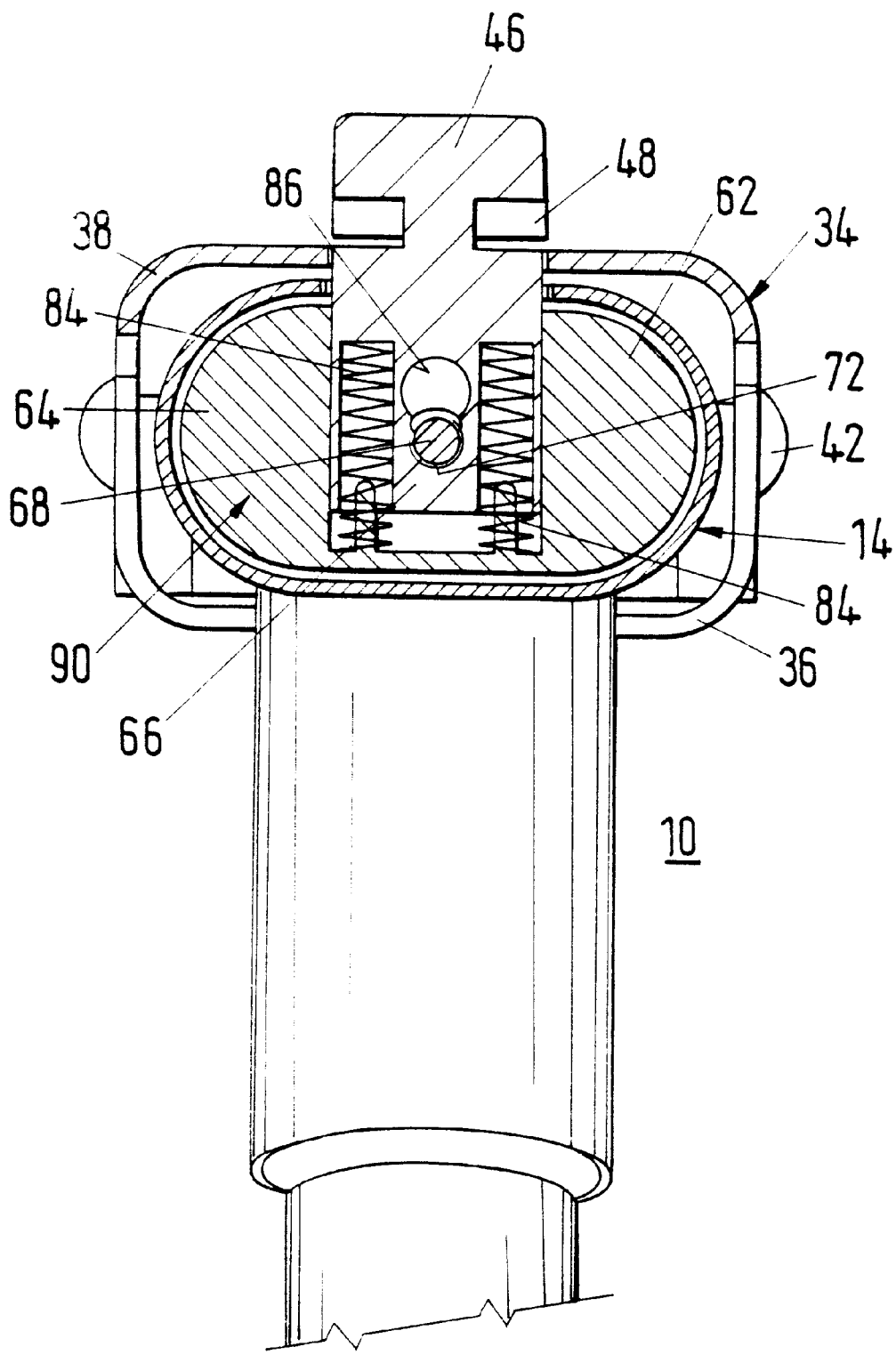

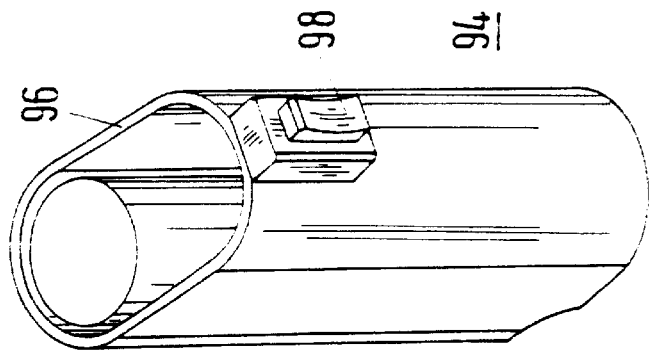
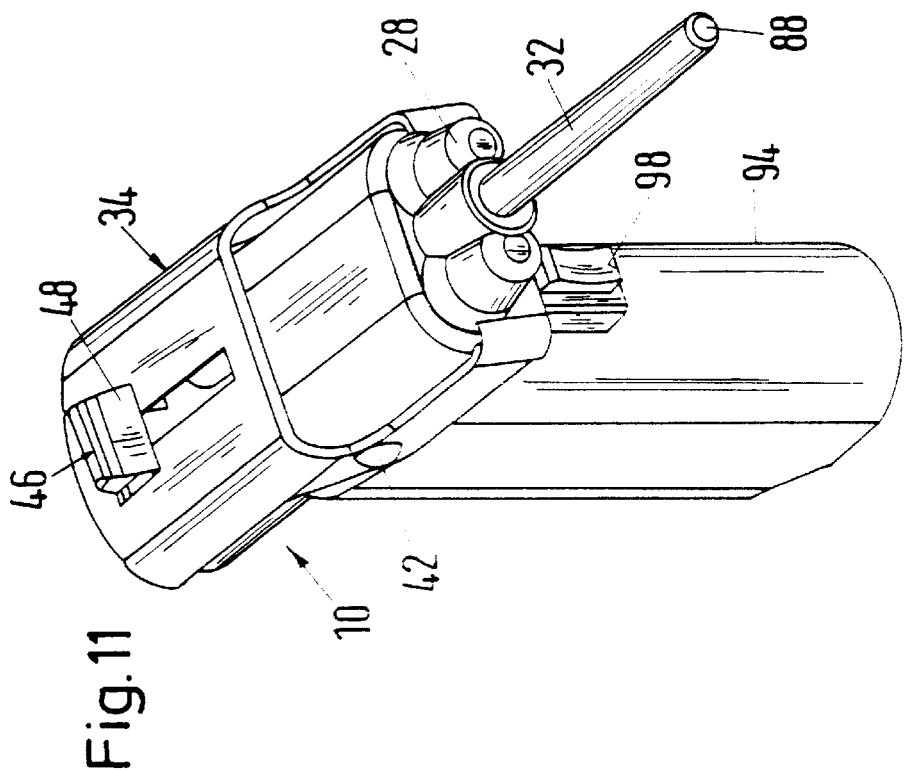

6,030,214

MANUAL DEVICE FOR DELIVERING A VISCOUS FLUID

TECHNICAL FIELD

The invention pertains to a manual device for delivering a viscous fluid.

BACKGROUND

A manual device for delivering viscous fluid is known from DE 31 03 610 A1, which is equipped with a rotation drive unit that is coupled to a gear assembly. Two piston rods having pistons are moved by way of the gear assembly and each act on a container that contains a viscous fluid of a multicomponent molding compound. The container is connected at its end opposite the piston to a mixing nozzle. The containers can each be removed from the manual device and exchanged. The gear assembly, to which the piston rod with the piston is connected, is driven by an electric motor provided in the manual device or by compressed air. In order to retract the piston into a starting position, a coupling/clutch is provided in each case between the piston rod and the gear assembly. This manual device is extremely heavy and because of the necessary compressed air seals, among other things, expensive to manufacture.

Furthermore, a stationary table device is known that has in a housing a piston to deliver the viscous fluid of the multicomponent molding compound as well as a gear assembly and rotation drive unit powering the piston via the gear assembly. The rotational drive unit can be controlled manually with regard to its rotational speed by way of a rotary switch seated in the housing. The amount of molding compound delivered per unit time is regulated by way of the rotational speed.

A disadvantage with such a design, when used in the dental field, is the inability for the device to be used directly on the patient, for instance, when an impression molding compound for dental purposes is to be delivered and mixed.

Furthermore, the dentist requires both hands for operating this device, one hand for the rotary switch and one hand for the bowl in which the mixed impression molding compound is placed. The handling is therefore extremely cumbersome and unfavorable for the field of dentistry and dental technician work.

A hand and angle piece for dental treatment purposes is known from DE 31 22 061 A1 that features a battery, an electric motor and a switch for turning the motor on and off. The hand and angle piece can be connected via a coupling/transmission to dental tools such as a drill, the tool comprising the opposing piece for the coupling of the hand and angle piece.

In DE 31 29 348 A1, a metering syringe is disclosed, which features a piston rod and piston arranged at the end of the piston rod in the cylindrical housing. The piston rod is provided with a thread that engages with a nut seated in a guidance part. With the revolution of the nut seated stationary in the guidance part the piston is moved via the piston rod in the housing.

SUMMARY OF THE INVENTION

The objects of the present invention address the problem of specifying a manual device for delivering a viscous fluid which, while avoiding the aforesaid disadvantages, can be used flexibly, is simple to handle and better meets the need of practice, particularly in the dental and dental technician field.

This problem is solved by the features of the present invention.

The invention is based on the recognition that by means of a construction in which the rotational drive unit can be separated from the patient, flexible design and powering possibilities result, which improve the handling and expand the possibilities of use.

According to the invention, the manual device for delivering a viscous fluid features at least one piston, which is seated in a housing having a handle, the piston acting on a container holding the viscous fluid, with a gear assembly for converting a rotational drive motion into a transitional motion of the piston and whose power input is connected to a rotational drive unit, wherein a coupling is provided between the rotational drive unit and the gear assembly for purposes of the optional connection of the manual device to different rotational drive units.

According to one embodiment of the invention, the manual device is constructed for delivering a multicomponent molding compound formed from viscous fluids, in which device at least two containers each having an individual component, are provided and the nozzle is part of a static mixer.

In particular, the coupling, such as an ISO coupling, is constructed for dental hand and angle pieces. In this way it is possible to utilize the present drive unit in any dental or dental technician practice by connecting the manual device via the coupling. The manual device can therefore forgo a special drive motor arranged in the housing and thus be offered considerably more economically.

According to one embodiment of the invention the axis of rotation of the rotation drive unit is arranged at an angle to the axis of the translational motion of the piston or to the plane spanned by two pistons arranged side-by-side. The angle is bridged by two meshing spur wheels. This guarantees a compact construction of small dimensions.

Electric or compressed-air motors of a dental unit as rotational drive units for hand and angle pieces with milling, drilling and grinding tools are in regular use for dental and dental technician practices for preparing teeth, crowns or the like. The rotational drive unit of the manual device therefore preferably comprises an electric or compressed-air motor and a coupling extension as part of the coupling for dental hand and angle pieces. Accordingly, the drive units already present in the dental field can be used with the manual device according to the invention without further effort. In particular, the motor is part of the dental unit in this case.

Alternatively, the rotational drive unit can also comprise a battery-operated motor if, for example, no dental motor is available. By way of the coupling, there can be exchanges between the battery-operated motor and the dental motor without further effort, which increases the range of use.

In order to be able to control the delivery rate of the multicomponent molding compound from the manual device in a simple manner, the motor interacts with a control unit. In this regard, the control unit features an actuation element constructed as a foot pedal. The adjustment of the motor speed and thus the delivery rate, as well as the turning on and off of the motor is done by foot, so that the dentist's/dental technician's hands remain free for treating and working on teeth, crowns or the like.

According to one embodiment of the invention, the gear assembly has an output shaft seated in the housing with a threaded section, where a nut connected to the piston engages with the threaded section.

A second coupling is preferably provided between the piston and the output shaft, in order to enable a retraction of the piston into a starting position.

According to one embodiment of the invention, the nut is part of the second coupling and the nut encloses the output shaft only in part. Adjoining the nut is a recess which is expanded in relation to the thread so that, upon movement of the second coupling in the direction of the nut, it is decoupled, together with the nut, from the shaft, and the output shaft is arranged in the recess. In that way the pistons can again be moved back into their original position after use of the manual device, whereby the maximum stroke motion of the piston and thus the maximum delivery motion of the piston is guaranteed for the next use.

In order to establish a base position, in which the nut engages with the thread of the output shaft, at least one spring is provided, which presses the nut with the coupling against the shaft.

In particular, a second spring is provided, which presses the coupling connected to the piston in the direction of the opening of the flow channel, whereby, first of all, the engagement of the nut with the thread of the output shaft is ensured, as well as enabling the locking of a mount holding the containers in the housing.

According to one embodiment of the invention, the gear assembly comprises a reduction gear assembly which preferably features a transmission ratio of 500 or 1000 to 1. In this way, the dental motors, which operate at high speeds, can be reduced to a rotational speed which is correct for the manual device in practice.

With the manual device according to the invention, the dentist can concentrate completely on the therapeutic field. He need neither exert manual force on the piston nor tie up one hand for adjusting the actuation element, since this can be done easily by way of the foot pedal.

Additional advantages and features are seen from the description below of several embodiments of the invention in conjunction with the drawings.

BRIEF DESCRIPTION OF THE DRAWINGS

FIG. 1 is a perspective view of the manual device according to one embodiment of the invention with film bags and static mixer not inserted in the receptacle;

FIG. 2 is a perspective detailed view of the constructive unit consisting of headpiece, static mixer and emptied film bags, the tip being angled off in this case;

FIG. 4 is a sectional view of the constructive unit consisting of static mixer, headpiece and the two film bags;

FIG. 5 is a cross sectional view through the manual device of FIG. 1;

FIG. 6 is an enlarged partial view of FIG. 5;

FIG. 7 is a sectional view of the pistons, the film bags, the headpiece and the static mixer of FIG. 5, wherein the film bags are partially emptied;

FIG. 8 is a longitudinal sectional view of the manual device;

FIG. 9 is a rear view of the manual device with a partial section;

FIG. 11 is a perspective view of the manual device with an alternative drive unit;

FIG. 12 is a perspective view of the housing of the drive unit of FIG. 11; and

DETAILED DESCRIPTION OF THE INVENTION

Figure 3:
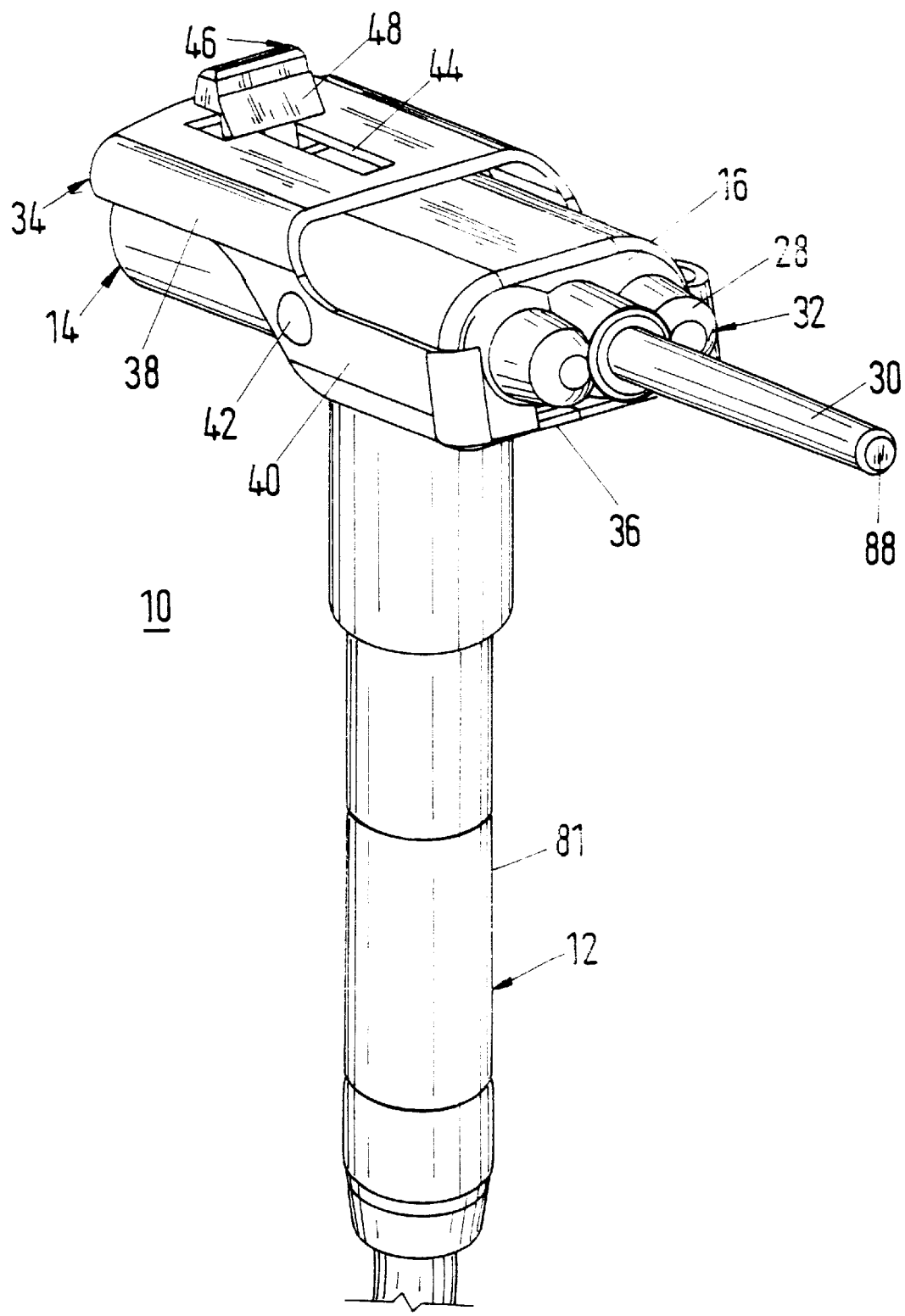
FIG. 3 is a perspective view of the manual device of FIG. 1 ready for operation.

In FIG. 1, a manual device 10 according to the invention is represented. The manual device 10 is connected to an electric-motor-powered rotational drive unit 12, that can be disconnected from the manual device 10 via a first coupling 82, (see FIG. 8), which interacts with a control unit not shown here. Alternatively to this, a lamellar motor operated by compressed air can also be used as the rotational drive unit.

The manual device 10 features a housing 14 that comprises a receptacle 16. The receptacle 16 consists of two mutually separated cylindrical chambers 18 and 20 which serve to accommodate film tubes 22 and 24.

A film tube 22,24 is closed off at each of its two ends with a clip 26; see FIGS. 4–7 as well, in which the tubes can be coated with TEFLON® (tetrafluoroethylene polymer) for better sliding out of the end of the respective film tube.

The two film tubes 22 and 24 contain components of a multicomponent molding compound, such as dental impression material, and are connected to a headpiece 28. The headpiece 28 features a static mixer 30 at its end situated away from the film tubes 22,24 which is permanently integrated into the headpiece 28 and projects in a rod shape from the latter in the direction of the film tubes 22,24.

The outer casing 31 of the static mixer 30 is constructed to be able to rotate against the base 29. In particular, an angled nozzle 33 arranged on the static mixer 30—FIG. 2—can be oriented in this way in the appropriate treatment positions, whereby when using the manual device, for instance, in conjunction with impression material in dental work, the application in the interproximal as well as in the lingual or buccal region is eased.

The film tubes 22 and 24, the headpiece 28, as well as the static mixer 30 constitute an inseparably connected constructive unit, which is removed from the manual device 10 after use and disposed of. In the following, this constructive unit is referred to as disposable unit 32.

The disposable unit 32 is inserted into the receptacle 16 such that the film tubes 22 and 24 engage with the associated chambers 18 and 20 and the headpiece 28 contacts the end face of the receptacle 16.

The disposable unit 32 can be secured in the receptacle by a holder 34.

The holder 34 can be pivoted about an axis which extends perpendicular to the longitudinal axis of the receptacle 16, or the chambers 18 and 20, and has a holder part 36 arranged underneath the receptacle 16 and a holder part 38 arranged above the receptacle 16.

The lower holder part 36 extends below the receptacle 16 past the receptacle 16 in the longitudinal direction of the receptacle 16 and surrounds in places the headpiece 28 of the disposable unit 32 inserted into the receptacle 16, see FIG. 3. In this way, the disposable unit 32 is secured in the housing 14 of the manual device 10.

To the side on the holder part 36, a bar 40 is provided, which extends with the holder 34 closed parallel to the receptacle 16 up to the articulation point 42 of the holder 34 on each side of the receptacle 16 and joins together the upper holder part 38 and the lower holder part 36. The lower holder part 36 thus extends from the articulation point 42 in the direction of the disposable unit 32, whereas the upper holder part 38 extends from the articulation point 42 in the direction of the side of the housing 14 remote from the disposable unit 32.

The holder 34 can be pivoted about its articulation points 42 from a closed position holding the disposable unit 32 inside the receptacle 16, FIG. 3, into an opening position releasing the disposable unit 32, FIG. 1, and back.

In the closed position the upper holder part 38 lies on top of the upper side of the receptacle 16 and the lower holder part 36, against the lower side of the receptacle 16.

A T-shaped cutout 44 is inserted into the upper holder part 38. The T-shaped cutout 44 is associated with a second coupling 46 and a catch 48, whose function in conjunction with the disposable unit 32, as will be discussed further below.

Figure 10:
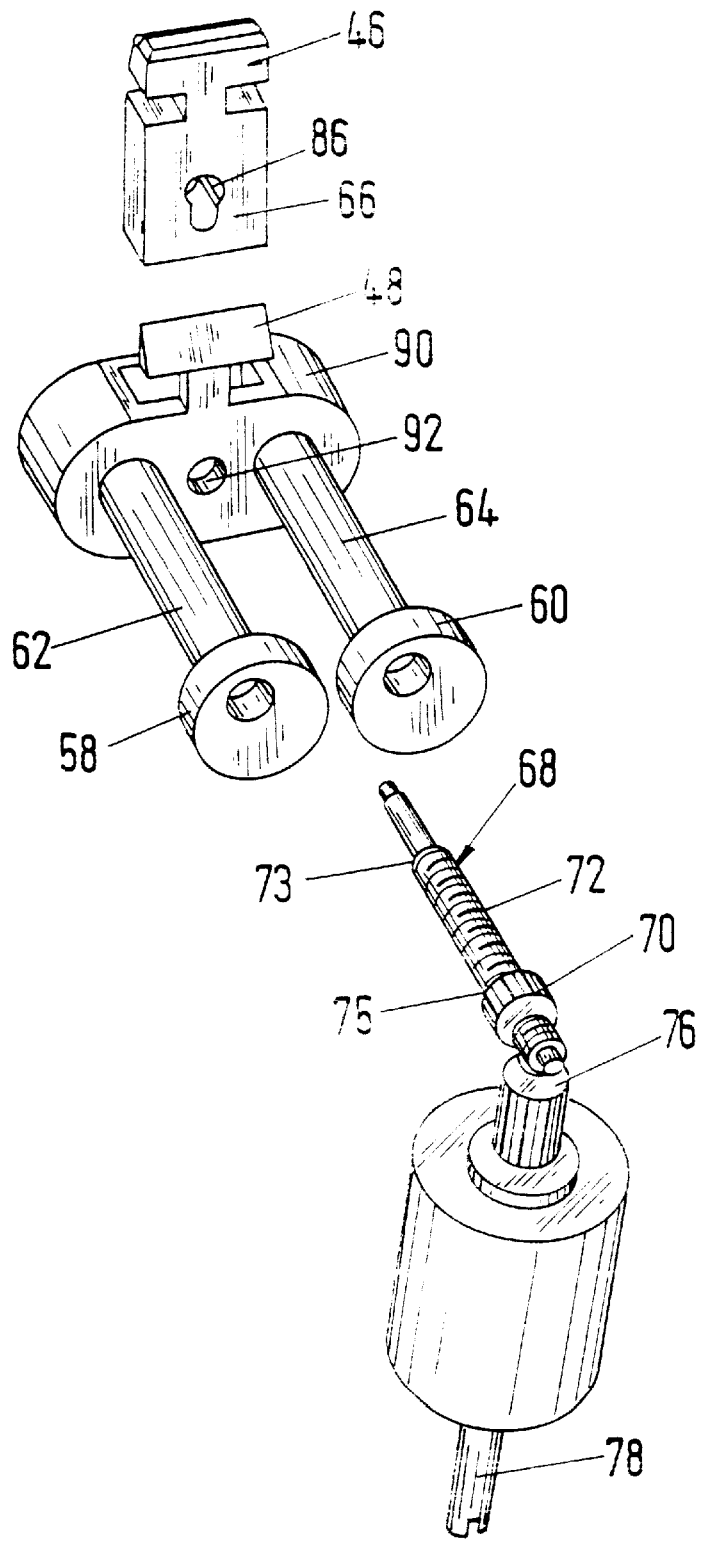
FIG. 10 is a perspective exploded view of the drive parts and pistons of the manual device of FIG. 1.

In front of the second coupling 46, a catch 48 is joined to an end piece 90—see FIGS. 8 and 10—which widens towards the bottom. With it the holder 34 is locked in its closed position. Parallel to the longitudinal axis of the receptacle 16, the end part 90, in which the second coupling 46 is inserted, is spring-loaded in the direction of the disposable unit 32—spring 74 according to FIG. 6—such that, upon closing the holder 34, the end part 90 is first moved via the catch 48 and the second coupling 46 first against the spring force by the upper holder part 36 backwards and, upon passing of the catch 48 through the cutout 44 of the holder 34, the second coupling 46 and the end part 90 with the catch 48 is again moved forward. A pivoting back of the holder 34 into the opening position is prevented by the catch 48.

After use of the manual device 10, the second coupling 46 and through it, the end part 90 with the catch 48 are pressed backwards against the spring force and the catch 48 can pass through the cutout 44 upon pivoting of the holder 34. The disposable unit 32 becomes free and can be exchanged.

A used disposable unit 32 is shown perspectively in FIG. 2, the static mixer 30 being equipped, as mentioned above, with an angled nozzle 33.

FIG. 4 shows the disposable unit 32 in section with filled film tubes 22 and 24. The film tubes 22,24 are closed off at their ends with the clip 26. A free end of the film tubes 22,24 engages with the headpiece 28, a ring 50 of the headpiece 28 being assigned to each film tube 22,24. The ring 50 is adapted to the shape of the filled film tube 22,24 and glued, welded or the like to the associated film tube 22,24.

The headpiece 28 has flow channels, initially constructed in a chamber shape, connecting the associated free ends of the film tubes 22 and 24 to the static mixer.

For each chamber of the flow channel 52, a screen 54 is placed in front of the static mixer 30 to prevent a penetration of the chambers 26 released from the film tubes 22,24 or of parts of the film tubes 22,24 into the static mixer 30.

The screen 54 associated with the respective chambers of the flow channel 52 is constructed in one piece with the static mixer 30. The static mixer 30 with the screen 54 is inserted into a drilled hole 56 in the headpiece 28 and glued to the headpiece 28 and thus inseparably connected to it. The screen 54 also extends over the entire cross section of the respective associated flow channel 52.

The static mixers 30 can have differing spirals, edges or the like in their passage openings, which permit a thorough mixing of the components passing through the static mixer 30 received from the film tubes 22,24 via the flow channel 52, for instance an impression-molding compound for dental purposes. Differing configurations of a static mixer 30 are used, depending on the consistency of the components. Such static mixers 30 are known and therefore not described in further detail.

The mixing ratio of the two components is 1:1 in the present case. It can also be different, however.

The components of the two film tubes 22 and 24 are only mixed together in the static mixer, that is, the flow channels 52 hold the two components separated until their entry into the static mixer 30. To this end, a separation wall 57 separating the two channels 52 is provided.

In its forward area, the housing 14 of the manual device 10 has the receptacle 16 having the cylindrical chambers 18,20. Seated in the rear area of the housing 14 are two piston rods 62,64, at the end of which a respective piston 58,60 is provided. A piston 58,60 impinges into a chamber 18,20, respectively. The piston 58,60 can each be moved parallel to the longitudinal axis of the receptacle 16 in the direction of the opening of the flow channel 52 pointed towards the film tubes 22 and 24. (See FIG. 5).

The piston 58,60 is connected via its piston rod 62,64 and the end part 90 connecting the two piston rods 62,64, see FIG. 10, to a nut 66 as part of the second coupling 46, since, as already explained, the second coupling 46 is arranged in the end part 90.

The piston 58,60 is adapted to the shape of the free end of the filled film tubes 22,24 pointing away from the headpiece 28 and surrounds the clip 26 closing off the film tube 22,24. This prevents the clip 26 from separating from the film tube 22,24 under rising internal pressure in the film tube 22,24.

Centered in the housing 14 between the receptacle 16 and the rear housing wall 67, a shaft 68 is seated, which features, in the area of the receptacle 16, a spur wheel 70 and, adjoining it and running away from the receptacle 16, thread 72 associated with the nut 66. The thread 72 is interrupted at the start of thread 73 and the end of thread 75, so that, upon reaching the beginning 73 or the end 75, the nut 66 is not moved any further by the shaft 68 with the thread 72. In this way damage to the manual device 10 is prevented.

The piston rod 62,64 and the end part 90 with the catch 48 is tensioned by a spring 74 in the direction of the film tubes 22,24. In this way, the catch 48 is held in a position that keeps the holder 34 in the closed position, as well as pressing the piston 58,60 against the associated film tube 22,24 as soon as the disposable unit 32 is inserted into the receptacle 16 of the housing 14. Additionally, the nut 66 is pressed against the end of the thread 72.

In FIGS. 5 and 6, the position is shown in which the second coupling 46 and the end part 90 with the catch 48 is pressed backwards for opening and closing the holder 34. As soon as the holder 34 is closed, the spring 74 presses the piston rod 62,64 in the direction of the headpiece 28, and the nut 66 engages with the thread 72. As the shaft 68 rotates, the nut 66, the piston rods 62 and 64, as well as the pistons 58 and 60 are moved towards the film tube 22 and 24, respectively.

An additional spur wheel 76 engages with the spur wheel 70. The additional spur wheel 76 is joined to the rotational drive unit 12, whose angle of rotation is arranged at an angle to the angle of translation of the two pistons 58 and 60, see FIG. 8.

In FIG. 8, a longitudinal section through the manual device 10 is shown, wherein the separating wall 57 separating the flow channels 52 in front of the static mixer 30 and the wall of the receptacle 16 which separates the two cylindrical chambers 18 and 20 are visible.

The additional spur wheel 76 is connected to the rotational drive unit 12 via an ISO coupling 82 for dental hand and angle pieces. It is also possible for other couplings for hand and angle pieces to be used. For this purpose, the opposing piece 78 of the ISO coupling engages with an ISO coupling extension of the first coupling 82 for dental hand and angle pieces, which is in turn connected to a dental motor 80 of a dentistry unit. Such dental motors are known in connection with hand and angle pieces with milling, drilling and grinding tools for dentistry purposes.

Via the first coupling 82 the manual device 10 can be simply and quickly detached from the dental motor 80 and the latter can be connected to a hand and angle piece for dentistry purposes.

The housing 81 of the dental motor 80, as well as the first coupling 82 and the part of the housing 14 of the manual device 10 facing downwards in regard to FIG. 8 together form a handle 79, with which the manual device 10 can be easily brought into the appropriate treatment positions for the patient. A reducing gear assembly 83 connecting the additional spur wheel 76 and the opposing piece 78 of the first coupling 82 and provided with a reduction ratio of 250 or 1000 to 1 is inserted into the handle 79.

In FIG. 9, a rear view of the manual device 10 with a partial section is shown, wherein the construction of the second coupling 46 is clarified in this illustration. The second coupling 46 is solidly seated in the end part 90 connecting the piston rods 62 and 64 and is movable in the vertical direction against the force of two springs 84.

In the lower area of the second coupling 46, the nut 66, which surrounds the shaft 68 in part, is provided. The springs 84 press the nut 66 against the shaft 68. Adjoining the nut 66, open towards the top, on the side opposite from the springs 84 is a cutout 86 which is made larger than the shaft 68.

In the position shown in FIG. 9, the nut 66 engages with the thread 72 of the shaft 68. As the drive motor 80 turns, the reduction gear assembly 83 and the spur wheel 76 are moved via the first coupling 82 and in turn drive the spur wheel 70 and thus the shaft 68. As the shaft 68 turns, the nut 66, together with the second coupling 46, the attached end part 90, the piston rods 62 and 64 and the pistons 58 and 60 attached to them are moved in the direction of the respective opening of the flow channels 52 facing the film tubes 22 and 24.

In parallel with this, the internal pressure in the film tubes 22 and 24 rises so strongly that the respective clips 26 detach from the film tubes 22 and 24 and the individual components in the film tubes 22 and 24 are pressed via the flow channels 52 into the static mixer 30 and are mixed there. The mixed substance, in the present case a two-component molding compound, for instance, an impression-molding compound for dentistry purposes, is discharged via the output nozzle 88.

Alternatively, the films of the film tubes 22,24 can be formed weakened in the end area, by laser material removal, for instance. The removal extends, for instance, in linear form nearly over the circumference, but not entirely. This has the effect that the broken end of the film tube 22,24 remains connected to the film tube 22,24. The screen 54 is therefore not closed off and the output of components from the film tubes 22,24 into the static mixer 30 is not hindered.

After use, the disposable unit 32 is removed in the prescribed manner from the manual device 10 and a new one with full film tubes 22 and 24 is inserted.

In order that the pistons 58 and 60 again have the complete stroke motion available for a newly inserted disposable unit 32, the second coupling 46 is pressed downwards against the springs 84. The shaft 68 is thereby arranged in the opening 86 of the nut 66. The second coupling 46 with the piston rods 62 and 64, as well as the pistons 58,60, can now be displaced against the force of the spring 74 in the direction of the rear housing wall 67. If the second coupling 46 is released, the nut 66 again engages with the thread 72 because of the force of springs 74 and 84 and can again move the pistons 58 and 60 against the film tubes 22,24 as the shaft 68 turns.

In FIG. 10, the motive parts are again shown individually in perspective exploded view. Here it becomes clear that the piston rods 62 and 64 engage with the shared end part 90, in which the second coupling 46 is seated, and that the end part 90 has the catch 48.

It ought to be clear that the drilled hole 92 illustrated in the end part 90 is larger than the shaft 68.

An alternative drive unit is shown in FIGS. 11 and 12, the manual device 10 being constructed otherwise in the manner already described. The drive unit 94 comprises a battery-driven motor seated in a motor housing 96, and likewise comprising a first coupling for hand and angle pieces 104. The motor housing 96 is constructed so as to accommodate batteries or storage batteries. The motor is controlled via a switch 98.

Figure 13:
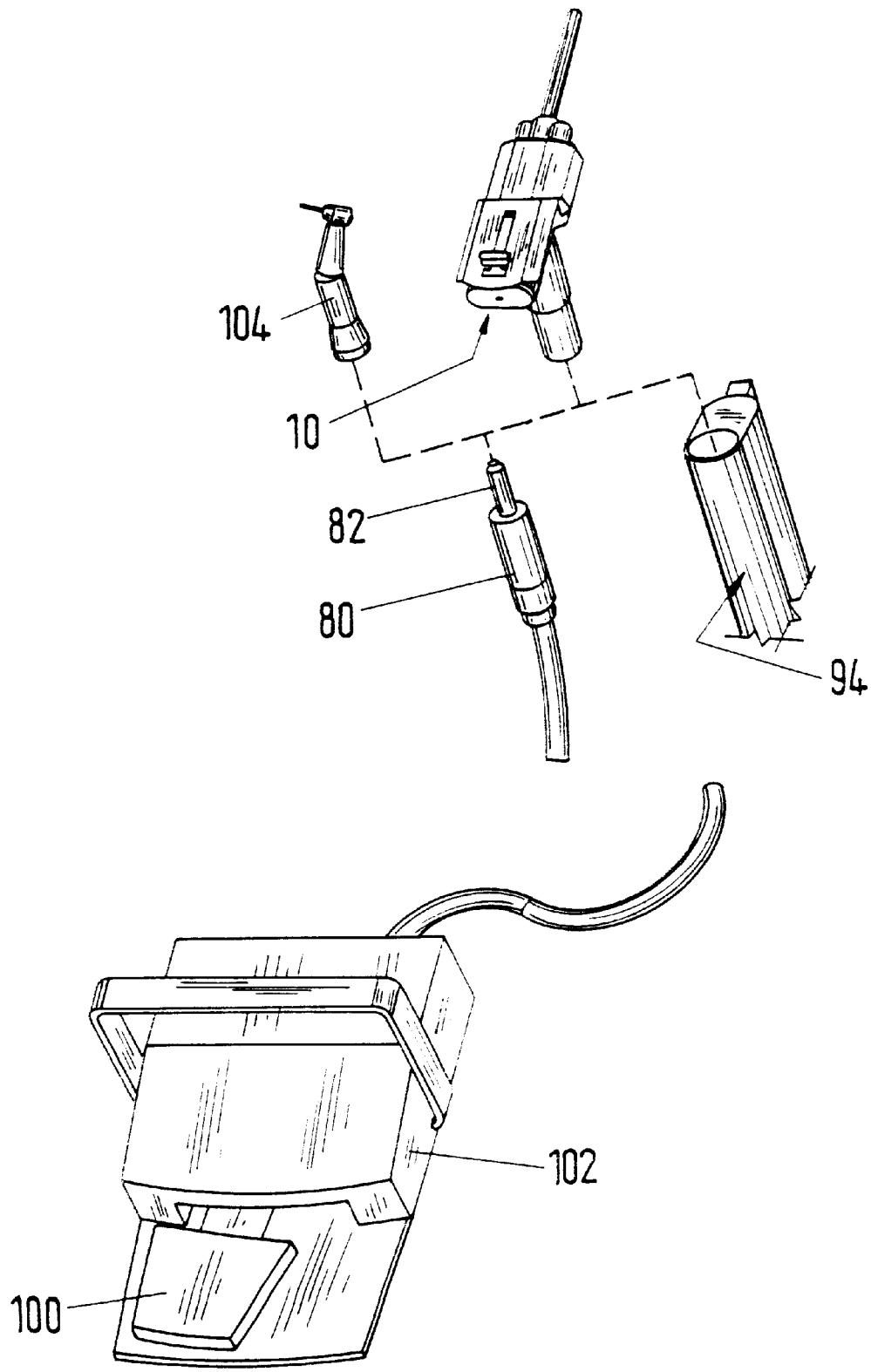
FIG. 13 is a perspective view of the different combination possibilities of the manual device.

The flexible design of the manual device 10 according to the invention becomes clear from FIG. 13. The dental motor 80 of a dentistry unit is connected to a control unit 102 featuring a foot pedal 100, with which the motor 80 is controlled. An angle piece 104 or the manual device 10 according to the invention can be connected to the first coupling 82 on the output side of the motor.

Thus impression-molding compounds that consist of two or more curable components can be applied by the dentist easily and in a sterile fashion with the manual device 10.

An additional advantage should also be seen in the fact that the dentist can control the amount of molding compound that can be delivered by way of the motor speed with the foot pedal 100, without a dentist's hand being needed or any force expended. The dentist can concentrate entirely on applying the molding compound to the part of the patient to be treated. Moreover, a dental motor already available in the practice is better utilized.

If a dental motor 80 is not available, recourse can be made to the battery-operated drive unit 94.

List of Reference Numbers

10 Manual device  
12 Rotational drive unit  
14 Housing  
16 Receptacle  
18 Chamber, left  
20 Chamber, right  
22 Film tube, left  
24 Film tube, right  
26 Clip  
28 Headpiece  
29 Base  
30 Static mixer  
31 Outer shell  
32 Disposable unit  
33 Nozzle  
34 Holder  
36 Holder part, lower  
38 Holder part, upper  
40 Bar  
42 Articulation point 44 Cutout
46 Second coupling
48 Catch
50 Ring
52 Flow channel
54 Screen
56 Drilled hole
57 Separating wall
58 Piston
60 Piston
62 Piston rod
64 Piston rod
66 Nut
67 Rear housing wall
68 Shaft/output shaft
70 Spur wheel
72 Thread
73 Start of thread
74 Spring
75 End of thread
76 Additional spur wheel
78 Opposing coupling piece
80 Dental motor
81 Motor housing
82 First coupling
83 Reduction gear assembly
84 Spring
86 Cutout
88 Delivery nozzle
90 End part
92 Drilled hole
94 Drive unit
96 Motor housing
98 Switch
100 Pedal
102 Control unit
104 Angle piece The invention is distinguished by its simple design and broad application possibilities. While preferred embodiments of the present invention has been shown and described, it will be understood by one skilled in the art that various changes or modifications can be made without varying from the scope of the invention.

I claim:

1. A manual device (10) for delivering a viscous fluid comprising a housing at least one piston (58, 60) seated in the housing (19) which has a handle (79), the piston acts on a container (22,24) having the viscous fluid therein, a gear assembly (70,72,78,83) for the conversion of a rotational drive motion into a translational motion of the piston (58, 60), the gear assembly connected to a rotational drive unit (12), a coupling (82) provided between the rotational drive unit (12) and the gear assembly (70,72,76,83).

2. The manual device of claim 1 further comprising at least two containers (22,24), each having an individual component of a multicomponent molding compound provided therein, a static mixer for mixing the individual components located in a discharge nozzle therefore.

3. The manual device according to claim 1 wherein the coupling (82) is constructed for mating with dental hand and angle pieces (104).

4. The manual device according to claim 1 wherein a rotational axis of the rotational drive unit (12) is arranged at an angle to an axis of the translational motion of the piston.

5. The manual device according to claim 4, characterized in that the angle is bridged by two spur wheels (70,76) engaging with one another.

6. The manual device according to claim 1 wherein a a rotational axis of the rotational drive unit (12) is arranged at an angle to a plane spanned by two pistons (58,60) arranged side-by-side.

7. The manual device according to claim 6, characterized in that the angle is bridged by two spur wheels (70,76) engaging with one another.

8. The manual device according to claim 1 wherein the rotational drive unit (12) is an electric or compressed-air motor for use in a dentistry unit, having a coupling extension (82) for mating with dental hand and angle pieces (104).

9. The manual device according to claim 1, wherein the rotational drive unit (12) is a battery-operated motor.

10. The manual device according to claim 1 further comprising a control unit (102) having an actuation element constructed as a foot pedal (100), the control unit interacting with the motor (80).

11. The manual device according to claim 1 further comprising an output shaft (68) of the gear assembly (70, 72,76,83) having a threaded section (72), a nut (66) connected to the piston (58,60) engaging the threaded section.

12. The manual device according to claim 11, further comprising a second coupling (46) provided between the piston (58,60) and the output shaft to permit a retraction of the piston into an initial position.

13. The manual device according to claim 12, wherein the nut (66) is part of the second coupling (46), the nut (66) engaging with the output shaft (68) only in some parts, a cutout (86) enlarged with respect to the thread (72), adjoins the nut (66), so that upon movement of the second coupling (46) in the direction of the nut (66), the nut is decoupled from the shaft (68) and the output shaft (68) is arranged in the cutout (86).

14. The manual device according to claim 13, further comprising at least one spring (84) which presses the nut (66) with the coupling (46) against the shaft (68).

15. The manual device according to claim 14, further comprising an additional spring (74) which presses the coupling (46) joined to the piston (58,60) in the direction of the opening of the flow channel (52).

16. The manual device according to claim 13, further comprising an additional spring (74) which presses the coupling (46) joined to the piston (58,60) in the direction of the opening of the flow channel (52).

17. The manual device according to claim 1 wherein the gear assembly (70,72,76,82) has a reduction gear (83) with a step-down ratio of 250 or 1000 to 1.

* * * * *